(12) United States Patent
Cronenberg (10) Patent No.: US 8,486,006 B2
(45) Date of Patent: Jul. 16, 2013

(54) MEDICAL INJECTOR WITH BUTTON ACTIVATION

(75) Inventor: Richard A. Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 51 days.

(21) Appl. No.: 13/063,849

(22) PCT Filed: Sep. 18, 2009

(86) PCT No.: PCT/US2009/057466
§ 371 (c)(1),
(2), (4) Date: Apr. 27, 2011

(87) PCT Pub. No.: WO2010/033795
PCT Pub. Date: Mar. 25, 2010

(65) Prior Publication Data
US 2011/0213299 A1    Sep. 1, 2011

Related U.S. Application Data

(60) Provisional application No. 61/192,467, filed on Sep. 18, 2008.

(51) Int. Cl.
*A61M 37/00* (2006.01)

(52) U.S. Cl.
USPC .................................. 604/82; 604/89; 604/90

(58) Field of Classification Search
USPC ............. 604/134–139, 131, 82–92, 518–520, 604/228, 208–211
See application file for complete search history.

(56) References Cited

U.S. PATENT DOCUMENTS

| | | | |
|---|---|---|---|
| 5,584,815 A | 12/1996 | Pawelka et al. | |
| 6,945,960 B2 | 9/2005 | Barker et al. | |
| 2002/0095120 A1* | 7/2002 | Larsen et al. | 604/187 |
| 2006/0111666 A1* | 5/2006 | Hommann et al. | 604/89 |

* cited by examiner

*Primary Examiner* — Nicholas Lucchesi
*Assistant Examiner* — Niyati D Shah
(74) *Attorney, Agent, or Firm* — Hoffmann & Baron, LLP (57) ABSTRACT

A medical injector is provided herein which includes a body; a slidable button at least partially disposed in the body; a displaceable plunger disposed in the body; a spring disposed to advance the plunger; and, a releasable retainer for retaining the plunger in a first state against force of the spring. Upon a predetermined extent of sliding movement of the button, the button engages the releasable retainer so as to cause the releasable retainer to release the plunger thus allowing the spring to advance the plunger. Advantageously, the subject invention provides a medical injector having an automated plunger drive which is triggered upon button activation, thereby minimizing premature or failed activations.

3 Claims, 7 Drawing Sheets

MEDICAL INJECTOR WITH BUTTON ACTIVATION

FIELD OF THE INVENTION

This invention relates to medical injectors, and, more particularly, to medical injectors having plunger drive mechanisms.

BACKGROUND OF THE INVENTION

Medical injectors are well known in the prior art, including injectors which have internal drive mechanisms for plunger advancement. Plunger advancement may be utilized to conduct automated reconstitution of a two-or more part medicament and/or to cause automated injection. More specifically, the automation of plunger advancement may be utilized to cause combination of a multiple part (e.g., wet/dry) medicament. In addition, or alternatively, the automated advancement of the plunger may cause a needle to be advanced for injection and/or medicament to be driven through the needle during injection. Such automated action requires a trigger mechanism. Concerns exist over premature or failed trigger activation.

SUMMARY OF THE INVENTION

A medical injector is provided herein which includes a body; a slidable button at least partially disposed in the body; a displaceable plunger disposed in the body; a spring disposed to advance the plunger; and, a releasable retainer for retaining the plunger in a first state against force of the spring. Upon a predetermined extent of sliding movement of the button, the button engages the releasable retainer so as to cause the releasable retainer to release the plunger thus allowing the spring to advance the plunger. Advantageously, the subject invention provides a medical injector having an automated plunger drive which is triggered upon button activation, thereby minimizing premature or failed activations.

These and other features of the subject invention will be better understood through a study of the following detailed description and accompanying drawings.

DETAILED DESCRIPTION OF THE INVENTION

With reference to the figures, a medical injector is shown and generally designated with the reference numeral 10. The medical injector 10 may he of various types, but preferably is of the pen injector type. The medical injector 10 may be used to administer various injectable liquids, particularly medicaments.

With reference to the figures, the medical injector 10 includes a body 12 and an axially-displaceable plunger 14 disposed therein. The plunger 14 may be formed as a single piece or modular components. The modular components may be fixed to one another or located adjacently, but not connected, so as to move together. A spring 16 is also provided configured and positioned to advance the plunger 14 a predetermined distance. Preferably, the spring 16 is a compression or coil spring, but other biasing elements may likewise he utilized. The spring 16 is preferably disposed between the plunger 14 and a portion of the body 12, such as cross-piece 18.

It is preferred that the plunger 14 be advanced in a distal direction. As used herein, distal refers to a direction towards a patient during use, while proximal refers to a direction away from a patient during use.

A releasable retainer 20 is provided configured and positioned to releasably retain the plunger 14 in an initial first state against the force of the spring 16. The releasable retainer 20 may include one or more deflectable latch tabs 22 preferably formed to extend outwardly from the plunger 14. Correspondingly, one or more ledges 24 are defined in the body 12.

The latch tabs 22 are inherently biased outwardly with the ledges 24 being positioned and configured to interferingly engage free ends 26 of the latch tabs 22 under force of movement of the spring 16. With this arrangement, distal advancement of the plunger 14 is limited due to interengagement between the latch tabs 22 and the ledge 24. The plunger 14, can, thus, be retained in an initial, first state before use.

A slidable button 28 is disposed in the body 12 to be movable relative thereto. The button 28 has a proximal end 30 which is accessible by a user. At least one arm 32, preferably two, extends distally from the proximal end 30 through corresponding openings 35 formed in the cross-piece 18, One or more outwardly biased tangs 37 may extend from the arms 32 configured to engage against the cross-piece 18 and resist proximal movement of the button 28.

The releasable retainer 20 is configured such that, the button 28 engages the releasable retainer 20 so as to cause the releasable retainer 20 to release the plunger 14 thereby allowing the spring 16 to advance the plunger 14. In particular, with sufficient distal advancement of the button 28, the arms 32 are shaped to telescope over a portion of the latch tabs 22 and, with sufficient distal advancement of the button 22, the arms 32 cause the latch tabs 22 to be inwardly deflected from the ledges 24, as shown in dashed lines in FIG. 3A. The arms 32 define a smaller diameter than the tabs 22 so that with sufficient distal displacement the arms 32 force the tabs 22 inwardly, The plunger 14 is then free to move distally.

The ledges 24 may be formed on the body 12. Alternatively, the ledges 24 may be formed on a component within the body 12, such as the interior sleeve described below. In addition, the location of the tabs 22 and the ledges 24 may be reversed so that the tabs 22 are located in the body 12 (on the body 12 itself or on a component therewithin) and that the ledges 24 are formed on the plunger 4. Various cooperating shapes of the elements may be utilized.

Figure 4:
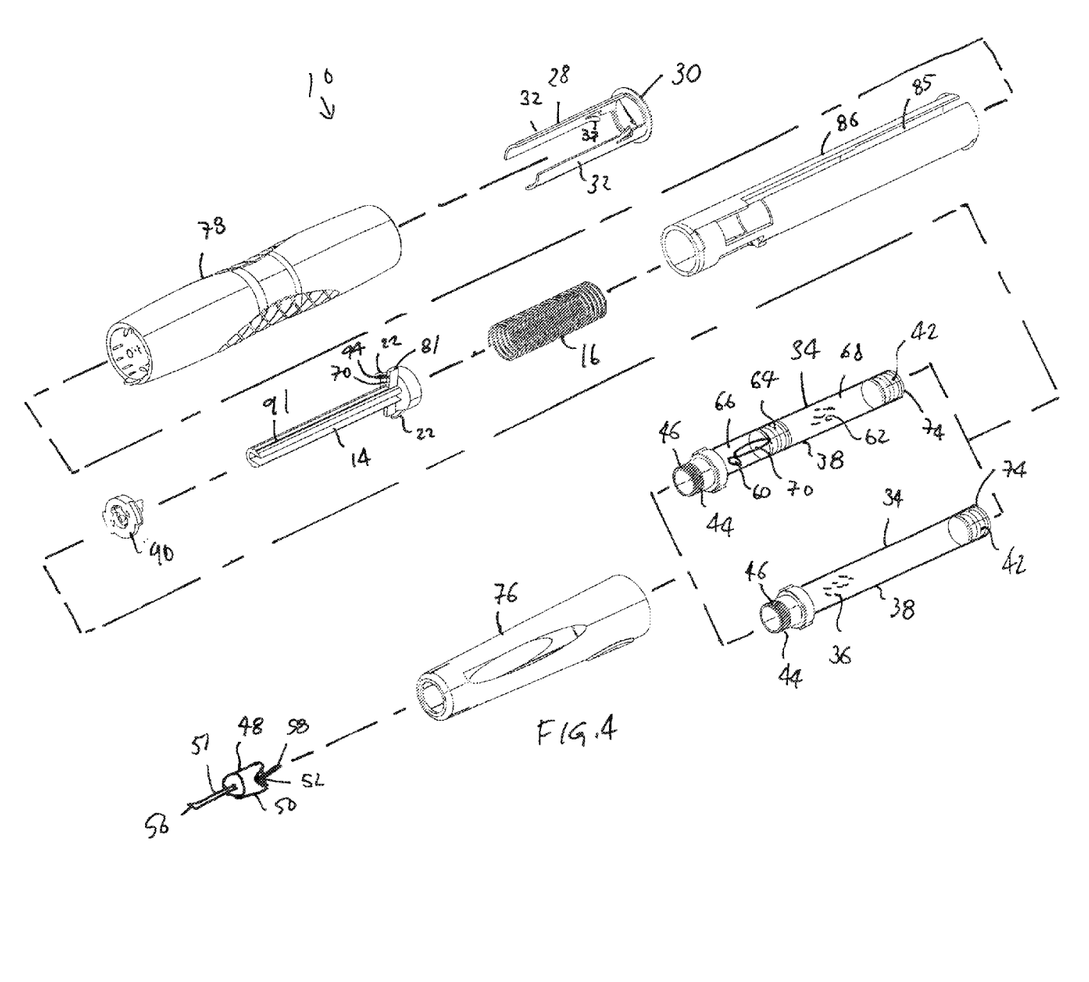
FIG. 4 is an exploded view of a medical injector formed in accordance with the subject invention.

The medical injector 10 includes a reservoir 34 disposed in the body 12 formed to accommodate medicament or other substance 36 for injection into a patient. As shown in FIG. 4, the reservoir 34 may be a single chamber disposed in a barrel 38 sealed at a proximal end by a septum 40 and sealed at a distal end by a stopper 42 which is formed to he slidable through the barrel 38 for urging the substance 36 therefrom, as known in the art. The medical injector 10 also includes a needle mounting surface 44 having features 46 formed thereon for mounting a needle 48 thereto. The needle 48 may include a hub 50 having mounting features 52 provided thereon for cooperative engagement with the features 46 in mounting the needle 48 to the needle mounting surface 44. The features 46 and the mounting features 64 may be of any known cooperating elements which permit a mechanical connection therebetween, such as threads or bayonet lock, and/or a frictional interengagement, such as a Luer mounting. The needle mounting surface 44 may be formed on the body 12 or a component thereof such as an adapter mounted to the barrel 38.

The needle 48 also includes a needle cannula 51 having a distal end 56, formed for insertion into a patient, and a proximal end 58.

The reservoir 34 may be configured to accommodate multiple components which are mixable for reconstitution. For example, as shown in FIG. 4, the reservoir 34 may accommodate first and second mixable components 60, 62. The stopper 42 may be associated with the reservoir 34 such that distal advancement of the stopper 42 over a predetermined distance shall cause mixing of the first and second mixable components 60, 62. Any known arrangement for allowing such mixing may be utilized. By way of non-limiting example, the first and second mixable components 60, 62 may be separated by a secondary stopper 64. The secondary stopper 64 divides the reservoir 34 into first and second chambers 66, 68, respectively, accommodating the first and second mixable components 60, 62. The septum 40 seals off the distal end of the first chamber 66, while the stopper 42 is positioned to seal off the proximal end of the second chamber 68. Preferably, if a dry component is used as one of the mixable components, the dry mixable component is located in the first chamber 66.

One or more by-pass channels 70 are formed in the wall of the reservoir 34. In an initial state, as shown in FIG. 4, the secondary stopper 64 is located at least partially proximally of the by-pass channels 70 so as to define a seal between the first and second chambers 66, 68 and to define a seal between the second chamber 68 and the by-pass channels 70. With distal advancement of the stopper 42, and with the second mixable component being wet and generally incompressible, force of movement of the stopper 42 is transmitted to the secondary stopper 64 through the second mixable component 62. With sufficient distal movement of the secondary stopper 64, the second chamber 68 comes into communication with the by-pass channels 70, thus allowing the second mixable component 62 to be urged into the first chamber 66 with further distal movement of the stopper 42. With sufficient distal advancement of the stopper 42, the second chamber 68 is collapsed with none or substantially none of the second mixable component 62 remaining therein. In addition, the secondary stopper 64 is located so as to define a seal between the first chamber 66 and the by-pass channels 70. The first and second mixable components 60, 62 are mixed within the first chamber 66, such as through agitation of the medical injector 10, so as to produce the injectable substance 36, ready for injection.

The barrel 38 of the reservoir 34 may be the barrel of a separate drug cartridge, as shown in the figures, or a portion of the medical injector 10, particularly the body 12.

As will be recognized by those skilled in the art, other arrangements for permitting reconstitution may be utilized. In addition, more than two-part systems, such as three-part and so forth, systems may be utilized. Active medical ingredients may be included in one or both of the first and second mixable components 60, 62. The first mixable component 60 may be dry (e.g., a powder or granular substance and/or a liquid (e.g., flowable (slurry or liquid)). As mentioned above, the second mixable component 62 is preferably only a wet flowable component, such as a liquid or slurry.

Distal advancement of the plunger 14 under force of the spring 16 may be used to achieve one or more objectives. The plunger 14 is configured to act against the stopper 42 and cause displacement thereof. With the reservoir 34 being configured for reconstitution, autoreconstitution of the contents of the reservoir 34 may be achieved. In addition, or alternatively, the medical injector 10 may be configured to be an autoinjector, where the needle 48 is initially housed within the body 12 and forced thereout of under force of the spring 16 so as to pierce a patient's skin, e.g., with forward movement of the reservoir 34, as known in the art. In addition, or alternatively, distal advancement of the plunger 14 may cause administration of the contents of the reservoir 34 through the injected needle.

Depending on the desired effect, the medical injector 10 may be configured to have the plunger 14 be driven a predetermined distance. A physical stop, such as interengagement between a stop 70 formed on the plunger 14 (which can be defined by one of more of the latch tabs 22 or the tabs 81) and a proximal end 74 of the reservoir 34 (e.g., proximal end of the barrel 38), may be employed to limit distal advancement of the plunger 14, Under certain circumstances, the plunger 14 may be distally advanced without the needle 48 being mounted to the medical injector 10. Thus, the reservoir 34 is not vented during such action. With the needle 48 being subsequently mounted to the reservoir 34, any residual gases trapped in the reservoir 34 are purged through the needle 48. It may be preferred to not provide a physical stop to the distal advancement of the plunger 14. In this manner, the contents of the reservoir 34 may be maximally compressed under force of the spring 16. With subsequent mounting of the needle 48 onto the medical injector 10, the reservoir 34 is vented thus permitting further distal advancement of the plunger 14. This secondary distal advancement may assist in priming the needle 48 for use.

The medical injector 10 may be a fixed dose injector configured to administer single or multiple fixed doses. In addition, the medical injector 10 may be configured to permit dose setting for either a single or multiple doses. In a preferred embodiment, the medical injector 10 is a single, variable-dose autoreconstitution injector.

Figure 1:
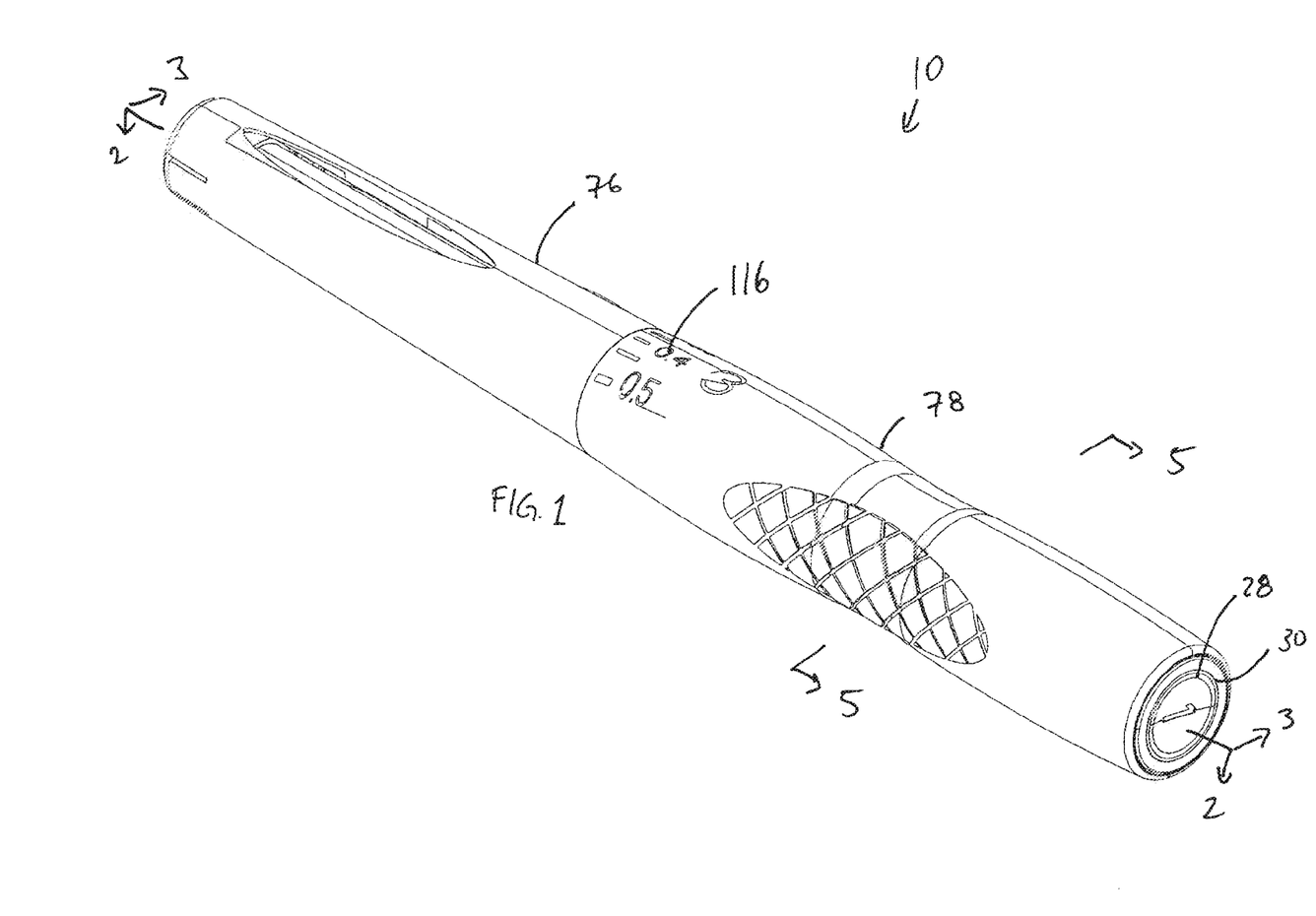
FIG. 1 is a perspective view of a medical injector formed in accordance with the subject invention.
Figure 2:
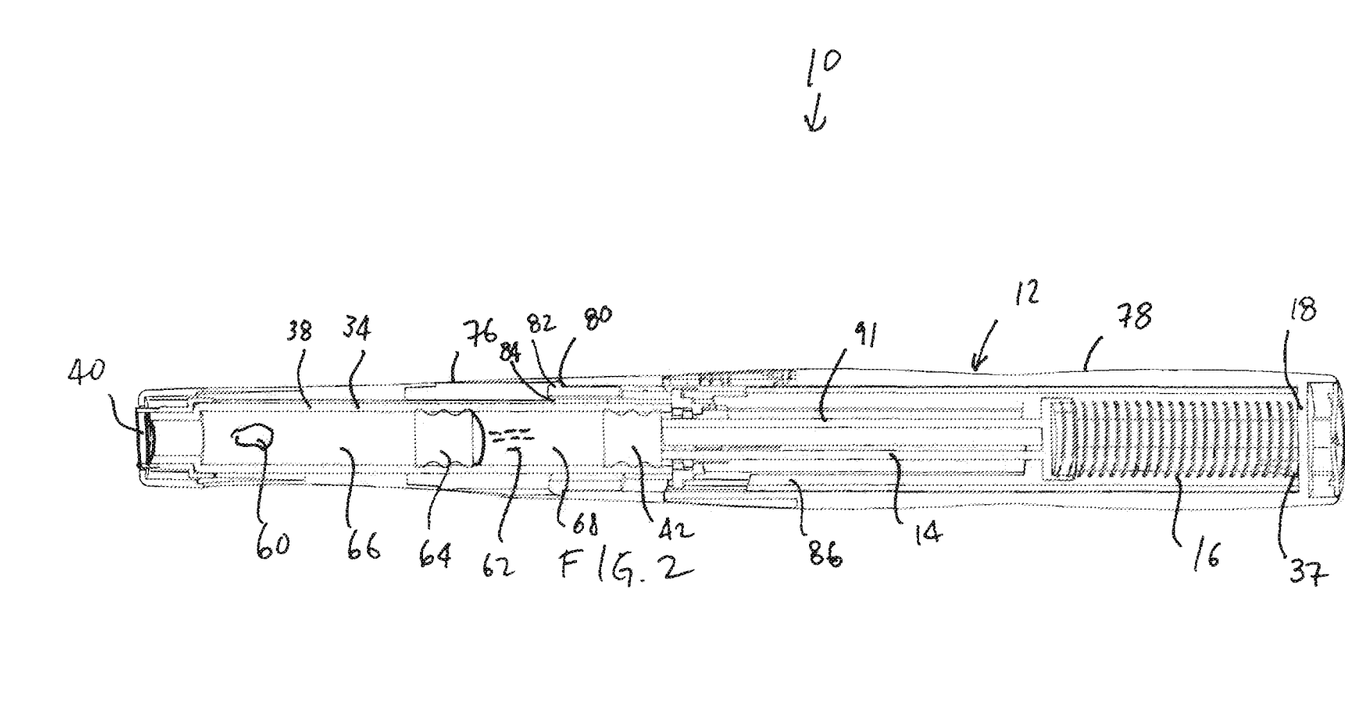
FIG. 2 is a cross-sectional view taken along line 2-2 of FIG. 1.

As will be appreciated by those skilled in the art, various configurations to permit dose setting may be utilized. It is preferred that the body 12 be formed of first and second body portions 76, 78 which are rotatably coupled. In this manner, relative rotation between the first and second body portions 76, 78 permits dose selection for the medical injector 10. Preferably, to obtain rotatability, as shown in FIG. 2, a track 80 is formed in one of the first and second body portions 76, 78, with one or more detents 82, formed opposite the track 80, being seated in the track 80 so as to lock the first and second body portions 76, 78 together once assembled. The detents 82 may be formed slidable along the track 80 so as to permit the first and second body portions 76, 78 to rotate relative to one another. One or more stops 84 may be located along the track 80 to limit the extent of relative rotation.

Figure 3:
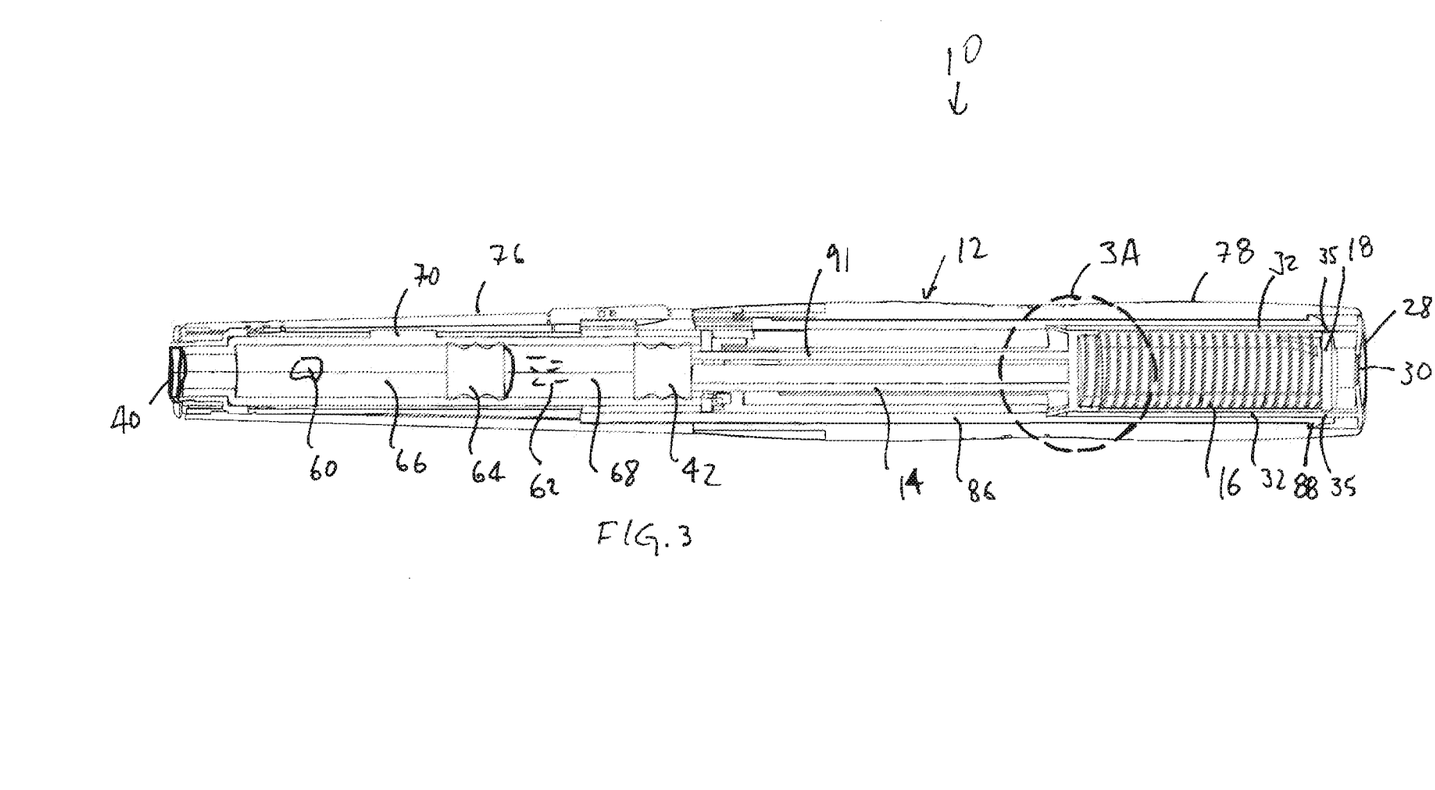
FIG. 3 is a cross-sectional view taken along line 3-3 of FIG. 1.
Figure 3A:
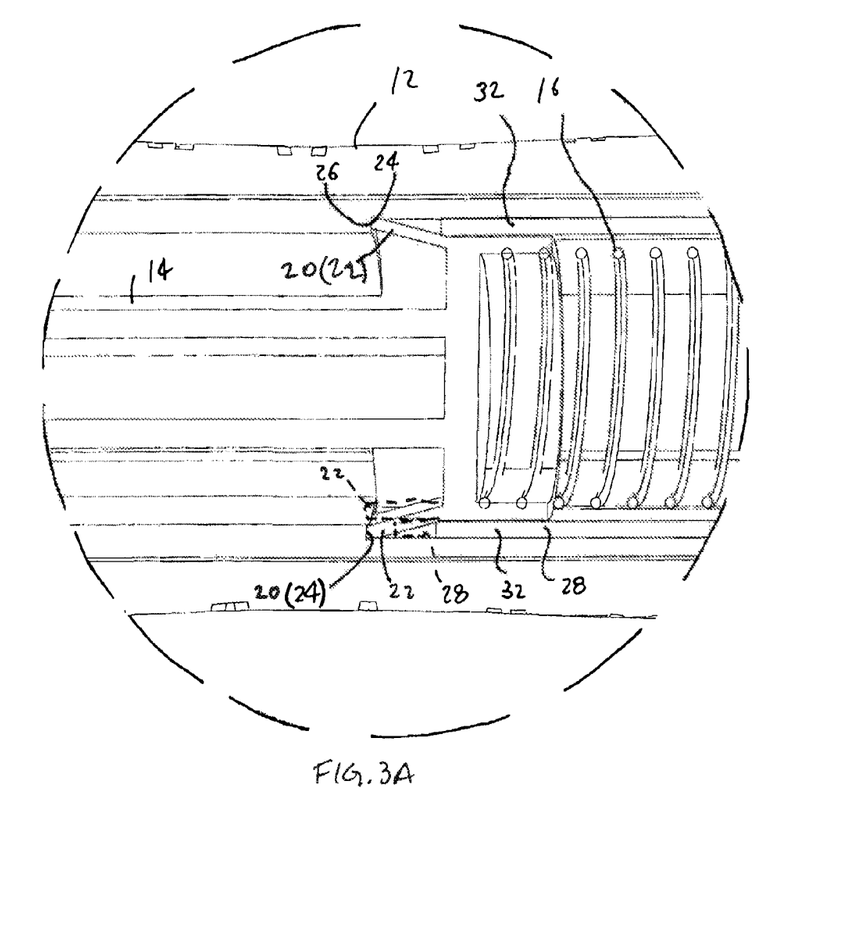
FIG. 3A is an enlarged section taken from FIG. 3.

In a preferred arrangement, with reference to FIGS. 2-4, the second body portion 78 may include an interior sleeve 86 on which the detents 82 are formed. It is preferred the interior sleeve 86 be non-rotatably coupled to the first body portion 76. The stops 84 may be provided on the first body portion 76 to prevent rotation. Li addition, it is preferred that the interior sleeve 86 be coupled to the second body portion 78 in any known manner so as to permit rotation of the second body portion 78 thereabout such as through mating snap fingers 88 coupled adjacent the cross-piece 18, particularly on the proximal side thereof. With the interior sleeve 86 being non-rotatably coupled to the first body portion 76, the interior sleeve 86 is held fixed with the second body portion 78 being rotatable thereabout.

Figure 5:
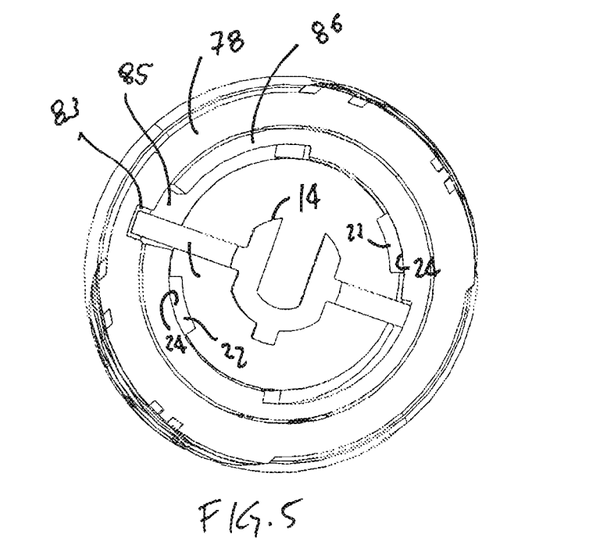
FIG. 5 is a cross-sectional view taken along line 5-5 of FIG. 1.

Preferably, for dose selection, the plunger 14 rotates with the second body portion 78. One or more tabs 81 may extend from the plunger 14 so as to be received in corresponding slots 83 formed in the second body portion 78, as shown in FIG. 5. By-pass slots 85 may be formed in the interior sleeve 86 which allow the tabs 81 to pass therethrough. The by-pass slots 85 may extend axially along the interior sleeve 86 so as to provide a straight-line path for distal advancement of the plunger 14.

For dose selection, and by way of non-limiting example, a dose ring 90 may he provided with a plurality of axially and radially spaced-apart abutment surfaces 92.

The abutment surfaces 92 are axially alignable with an engagement surface 94 formed on the plunger 14 such that with sufficient distal displacement of the plunger 14 at least one of the abutment surfaces 92 will be caused to be engaged by the engagement surface 94 thus limiting the stroke of the plunger 14. The engagement surface 94 may be defined on one or more of the tabs 81. With this arrangement, a controlled amount of distal displacement of the plunger 14 may be transmitted to the stopper 42. Stem 91 of the plunger 14 passes through opening 93 of the dose ring 90 to obtain proper alignment of the engagement surface 94 with the corresponding abutment surface 92 and so that the stem 91 may engage the stopper 42. Moreover, stroke length corresponding to the movement of the plunger 14 may be adjusted depending on the abutment surface 92 which is in engagement with the engagement surface 94. The greater the initial distance of the abutment surfaces 92 from the engagement surface 94, the corresponding greater dose that will be caused to be administered. Regardless of the selected dose amount, it is preferred that the plunger 14 have a fixed length of stroke for distal displacement during administration of an injection. The further abutment surfaces 92 provide greater distal movement of the plunger 14. The extent of movement of the plunger 14 dictates the extent of movement of the stopper 42 and, thus, dictates the amount of the injectable solution 36 to be driven from the reservoir 34 in an injected dose. The dose ring 90 is preferably stationary. A spring arm 120 may extend from the dose ring 90 to resiliently press against the plunger 14 and provide stability thereto.

Figure 6:
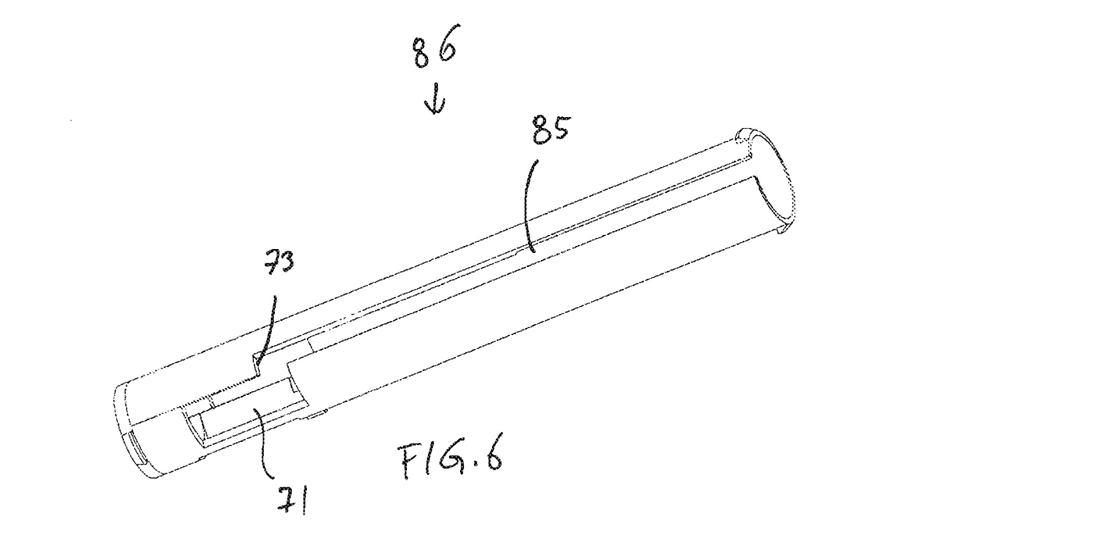
FIG. 6 shows an interior sleeve useable with the subject invention.
Figure 7:
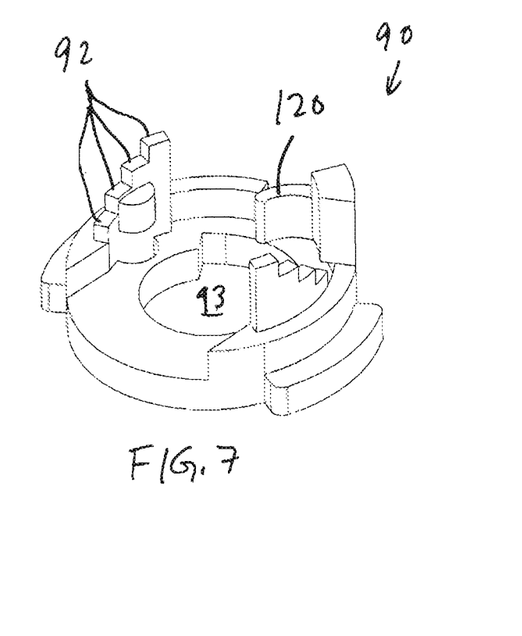
FIG. 7 is a perspective view of a dose ring useable with the subject invention; and, FIG. 8 is a schematic showing an arrangement for restricting radial motion.

The dose is selected by rotating the second body portion 78 which is fixed to the plunger 14 so as to rotate therewith. To prevent the second body portion 78 from setting a dose prior to proper preparation of the medical injector 10, such as prior to mixing of the mixable components 60, 62, rotation of the plunger 14 may be limited by interengagement of the tabs 81 with the by-pass slots 85. As shown in FIG. 6, open space 71 may be defined at he distal terminus of the by-pass slots 85 which extends radially to permit rotation of the tabs 81 thereinto. The open space 71 may be defined by an enlarged diameter portion of the interior sleeve 86 which is of limited depth in the wall of the interior sleeve 86 or extends completely therethrough. In this manner, doses can be adjusted by rotating the plunger 14 to axially locate the engagement surface 94 with a desired of the abutment surfaces 92. The by-pass slots 85 may be formed with one or more catches 73 which initially catch the tabs 81 upon distally advancing the predetermined distance and prior to dose setting. By permitting radial adjustment at the terminus of the by-pass slots 85, dose setting may be restricted to post-advancement of the plunger 14.

Figure 8:
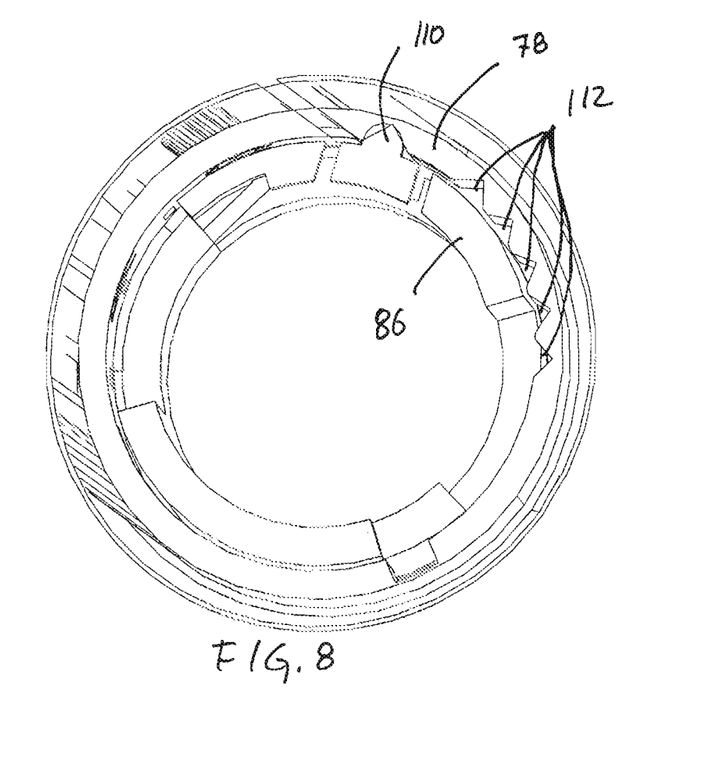

It is preferred that the second body portion 78 be releasably retained in positions corresponding to the various dose settings. In this manner, it is preferred that once a dose has been set, there is no inadvertent rotation of the second body portion 78, thus avoiding that an improper of the abutment surfaces 92 engage the engagement surface 94. Such an arrangement is disclosed in U.S. Pat. No. 6,793,646. As shown in U.S. Pat. No. 6,793,646, with reference to FIG. 8, one or more tabs 110 may be formed on the interior sleeve 86 which are selectively engageable with one or more ratchet teeth 112 formed on the second body portion 78. The ratchet teeth 112 may be circumferentially spaced apart and positioned to represent dose settings corresponding to the abutment surfaces 92. The tabs 110 nest in between the ratchet teeth 112 at given radial positions of the plunger 14 corresponding to different dose sizes. With turning of the second body portion 14, the tabs 110 are caused to by-pass the ratchet teeth 112. The ratchet teeth 112 maintain the radial position of the second body portion 78.

In addition, it is preferred that the plunger 14 be limited in axial movement so as to permit a fixed stroke length of distal advancement for dose administration. The stroke of an injection is defined by the extent of distal movement of the plunger 14. The plunger 14 may be advanced in any known manner for injection, including under force of movement of the spring 16.

Indicia 116 may be provided to represent doses. The indicia 116 may include numeral representations and a pointer or other indicator. The indicia 116 may be on both the first and second body portions 76, 78 to provide dose indications during relative rotation therebetween in dose setting.

What is claimed is:

1. A medical injector comprising:
   a body;
   a slidable button at least partially disposed in said body;
   a displaceable plunger disposed in said body;
   a spring disposed to advance said plunger; and,
   a releasable retainer for retaining said plunger in a first state against force of said spring, wherein, upon a predetermined extent of sliding movement of said button within said body, said button engages said releasable retainer so as to cause said releasable retainer to release said plunger thus allowing said spring to advance said plunger,
   wherein said releasable retainer includes at least one latch tab extending from said plunger and at least one ledge formed in said body, said ledge interferingly engaging said latch tab to retain said plunger in said first state, and
   wherein, upon said predetermined extent of sliding movement of said button, said button telescopes over said at least one latch tab and causes inward deflection of said latch tab so as to come out of interfering engagement with said ledge thus allowing said spring to advance said plunger.

2. The medical injector as in claim 1, further comprising a reservoir disposed in said body, said reservoir accommodating first and second mixable components, said first and second mixable components being mixed with advancement of said plunger.

3. The medical injector as in claim 2, further comprising a stop formed on said plunger configured to retain said plunger in a second state after advancement of a predetermined distance.

* * * * *

UNITED STATES PATENT AND TRADEMARK OFFICE
CERTIFICATE OF CORRECTION

PATENT NO. : 8,486,006 B2  Page 1 of 1
APPLICATION NO. : 13/063849
DATED : July 16, 2013
INVENTOR(S) : Richard A. Cronenberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 91 days.

Signed and Sealed this
Eighth Day of September, 2015

Michelle K. Lee
*Director of the United States Patent and Trademark Office*